US006190407B1

(12) United States Patent
Ogle et al.

(10) Patent No.: US 6,190,407 B1
(45) Date of Patent: Feb. 20, 2001

(54) MEDICAL ARTICLE WITH ADHERED ANTIMICROBIAL METAL

(75) Inventors: Matthew F. Ogle; William R. Holmberg, both of St. Paul; Richard F. Schroeder, Oakdale; Donald S. Guzik, White Bear Lake; M. William Mirsch, II, Roseville; Darrin J. Bergman, Shoreview; Hallie A. Finucane, Arden Hills; Katherine S. Tweden, Mahtomedi, all of MN (US)

(73) Assignee: St. Jude Medical, Inc., St. Paul, MN (US)

(*) Notice: Under 35 U.S.C. 154(b), the term of this patent shall be extended for 0 days.

(21) Appl. No.: 09/224,178

(22) Filed: Dec. 31, 1998

Related U.S. Application Data

(63) Continuation of application No. 09/143,989, filed on Aug. 31, 1998, which is a continuation-in-part of application No. 08/974,992, filed on Nov. 20, 1997.

(51) Int. Cl.$^7$ .................................................. A61F 2/06
(52) U.S. Cl. .................. 623/1.51; 623/1.54; 623/23.57; 427/2.31; 427/455; 604/265
(58) Field of Search ............................ 623/11, 1, 2, 12, 623/66, 901, 1.5, 1.51, 1.54; 606/76; 604/265; 427/2.24, 2.31, 455

(56) References Cited

U.S. PATENT DOCUMENTS

| | | |
|---|---|---|
| 4,054,139 | 10/1977 | Crossley . |
| 4,253,463 | 3/1981 | Kim . |
| 4,411,041 | 10/1983 | Braga . |
| 4,411,648 | 10/1983 | Davis et al. . |
| 4,418,686 | 12/1983 | Child . |
| 4,456,589 | 6/1984 | Holman et al. . |
| 4,476,590 | 10/1984 | Scales et al. . |
| 4,479,795 | 10/1984 | Mustacich et al. . |
| 4,483,688 | 11/1984 | Akiyama . |
| 4,563,485 | 1/1986 | Fox, Jr. et al. . |
| 4,564,361 | 1/1986 | Akiyama . |
| 4,569,673 | 2/1986 | Tesi . |
| 4,581,028 | 4/1986 | Fox, Jr. et al. . |
| 4,592,920 | 6/1986 | Murtfeldt . |
| 4,603,152 | 7/1986 | Laurin et al. . |
| 4,612,337 | 9/1986 | Fox, Jr. et al. . |
| 4,615,705 | 10/1986 | Scales et al. . |
| 4,846,844 | 7/1989 | DeLeon et al. . |
| 4,847,049 | 7/1989 | Yamamoto . |
| 4,886,505 * | 12/1989 | Haynes et al. .................. 604/265 |
| 4,902,503 | 2/1990 | Umemura et al. . |
| 4,923,450 | 5/1990 | Maeda et al. . |
| 4,933,178 | 6/1990 | Capelli . |
| 4,973,320 | 11/1990 | Brenner et al. . |
| 5,019,096 | 5/1991 | Fox, Jr. et al. . |
| 5,049,139 | 9/1991 | Gilchrist . |
| 5,049,140 | 9/1991 | Brenner et al. . |
| 5,059,186 | 10/1991 | Yamamoto et al. . |
| 5,207,706 * | 5/1993 | Menaker ........................... 623/1 |
| 5,295,979 | 3/1994 | DeLaurentis et al. . |
| 5,320,908 | 6/1994 | Sodervall et al. . |
| 5,324,275 | 6/1994 | Raad et al. . |
| 5,368,608 | 11/1994 | Levy et al. . |
| 5,409,467 | 4/1995 | Raad et al. . |
| 5,454,886 | 10/1995 | Burrell et al. . |
| 5,468,562 | 11/1995 | Farivar et al. . |
| 5,474,797 | 12/1995 | Sioshansi et al. . |
| 5,492,763 | 2/1996 | Barry et al. . |
| 5,498,248 | 3/1996 | Milder . |
| 5,516,480 | 5/1996 | Krall et al. . |
| 5,520,664 | 5/1996 | Bricault, Jr. et al. . |
| 5,622,746 * | 4/1997 | Hanh et al. ........................... 427/79 |
| 5,630,804 | 5/1997 | Imada et al. . |
| 5,662,913 | 9/1997 | Capelli . |
| 5,672,325 * | 9/1997 | Hiratsuka et al. .................. 423/210 |

FOREIGN PATENT DOCUMENTS

| | | |
|---|---|---|
| 0 190 504 | 8/1986 | (EP) . |
| 0 206 024 | 12/1986 | (EP) . |
| 0 328 421 | 8/1989 | (EP) . |
| 0 516 184 A1 | 12/1992 | (EP) . |
| 0 596 615 A1 | 5/1994 | (EP) . |
| WO 93/07924 | 4/1993 | (WO) . |
| WO 96/01119 | 1/1996 | (WO) . |
| WO 97/27886 | 8/1997 | (WO) . |

OTHER PUBLICATIONS

"A Prospective Randomized Trial Comparing the Silver–Impregnated Collagen Cuff With the Bedside Tunneled Subclavian Catheter" by Babycos et al., Journal of Parenteral and Enteral Nutrition, vol. 17, No. 1, pp. 61–63 (1993).

"Frequency, Therapy, and Prevention of Infections Associated with Large Bore Catheters" by R. Bambauer et al., ASAIO Journal, vol. 38, No. 2, pp. 96–101 (1992).

"New Surface–Treatment Technologies for Catheters Used for Extracorporeal Detoxification Methods" by Bambauer et al. Dialysis & Transplantation, vol. 24, No. 5, pp. 228–237 (May 1955).

"The Treatment of Large Cutaneous Burns with Silver Creams" by, Butcher, Jr. et al., The Journal of Trauma, vol. 9, No. 5, pp. 359–376 (1969).

"Efficacy and Duration of Antistaphylococcal Activity Comparing Three Antibiotics bonded to Dacron Vascular grafts with A Collagen Release System" by Chervu et al., Journal of Vascular Surgery, vol. 13, pp. 897–901 (1991).

(List continued on next page.)

*Primary Examiner*—David H. Willse
*Assistant Examiner*—Choon P. Koh
(74) *Attorney, Agent, or Firm*—Hallie A. Finucane, Esq.; Westman, Champlin & Kelly, P.A.; Peter S. Dardi

(57) ABSTRACT

A variety of new ways can be used for associating antimicrobial elemental metal with a medical article. The associated antimicrobial metal reduces the risk of infection associated with the medical use of the medical article. New medical articles are produced by some of these new approaches. Some of the methods involve ways of adjusting the dissociation rate of associated elemental metal such that desired degrees of antimicrobial activity can be achieved over selected periods of time.

12 Claims, No Drawings

OTHER PUBLICATIONS

"Antibacterial Vascular Grafts With Improved Thromboresistance" by Clark et al., Arch. Surg., vol. 109, pp. 159–162 (Aug. 1974).

"Results of a Multicenter Outpatient Burn Study on the Safety and Efficacy of Dimac–SSD, a New Delivery System for Silver Sulfadiazine" by, Deitch et al., The Journal of Trauma, vol. 29, No. 4, pp. 430–434 (Apr. 1989).

"Photochemical Coatings for the Prevention of Bacterial Colonization" by Dunkirk et al., Journal of Biomaterials Applications, vol. 6, pp. 131–156 (Oct. 1991).

"Rifampicin Antibiotic Impregnation of The St. Jude Medical Mechanical Valve Sewing Ring: A Weapon Against Endocarditis" by French et al., The Journal of Thoracic and Cardiovascular Surgery, vol. 112. No. 2, pp. 248–252 (Aug. 1996).

"The Antibacterial Effect of Treating Sutures with Silver" by Gravens et al., Surgery, vol. 73, No. 1, pp. 122–127 (Jan. 1973).

"Silver and Its Compounds" by Grier, Nathaniel, in Disinfection, Sterilization, and Preservation, Chapter 20, pp. 395–407.

"Antibacterial Silver Surfaces—An Assessment of Needs and Opportunities For Clinical Devices" by Haynes, et al., Proceedings of the First International Conference on Gold and Silver in Medicine, Bethesda, Maryland, pp. 331 (Abstract), May 13–14, 1987.

"In Vitro Evaluation of the Antimicrobial Efficacy and Biocompatibility of a Silver—Coated Central Venous Catheter" by Jansen et al., Journal of Biomaterials Applications, vol. 9, pp. 55–70 (Jul. 1994).

"Antibiotic–Bonded PTFE Vascular Grafts: The Effect of Silver Antibiotic on Bioactivity following Implantation" by Kinney et al., Journal of Surgical Research, vol. 50, pp. 430–435 (1991).

"Assessment of Silver–coated Urinary Catheter Toxicity by Cell Culture" by Liedberg et al., Urol. Res., vol. 17, pp. 359–360 (1989).

"Catheter Induced Urethral Inflammatory Reaction and Urinary Tract Infection" by Liedberg et al., Scandinavian Journal of Urology and Nephrology, Suppl. No. 124, pp. 1–43 (1989).

"Surface Antimicrobial Activity of Heparin–Bonded and Antiseptic–Impregnated Vascular Catheters" by Mermel et al., The Journal of Infectious Diseases, vol. 167, pp. 920–924 (Apr. 1993).

"Biocompatibility of Silver–Coated Polyurethane Catheters and Silver–Coated Dacron material*" by Oloffs et al., Biomaterials, vol. 15, No. 10, pp. 753–758 (1994).

"A Large Randomized Clinical Trial of a Silver–Impregnated Urinary Catheter: Lack of Efficacy and Staphylococcal Superinfection" by Riley et al., The America Journal of Medicine, vol. 98, pp. 349–356 (Apr. 1995).

"An Experimental Study on Silver in the Nervous System and on Aspects of Its General Cellular Toxicity" by Rungby, Jorgen, Danish Medical Bulletin, vol. 37, No. 5, pp. 442–449 (Oct. 1990).

"New Processes for Surface Treatment of Catheters" by Sioshansi, Piran, Artificial Organs, vol. 18, No. 4, pp. 266–271 (1994).

"Reduced Bacterial Colonization of External Fixation Pins" by Tobin et al., Surfaces in Biomaterials, pp. 19–22 (1995).

"Biocompatibility of Silver–Modified Polyester for Antimicrobial Protection of Prosthetic Valves" by Tweden et al., J. Heart Valve Dis., vol. 6, No. 5, pp. 553–561 (Sep. 1997).

* cited by examiner

MEDICAL ARTICLE WITH ADHERED ANTIMICROBIAL METAL

CROSS REFERENCE TO RELATED APPLICATIONS

This application is a continuation of U.S. application Ser. No. 09/143,989 filed on Aug. 31, 1998, which is a continuation-in-part of U.S. patent application Ser. No. 08/974,992, filed on Nov. 20, 1997, entitled "MEDICAL ARTICLE WITH ADHERED ANTIMICROBIAL METAL," the disclosure of which is incorporated herein by reference in its entirety.

FIELD OF THE INVENTION

The invention relates to medical articles having associated antimicrobial metal. Furthermore, the invention relates to new approaches for applying antimicrobial metal to a variety of biocompatible materials.

BACKGROUND OF THE INVENTION

A variety of medical articles are designed particularly for contact with a patient's bodily fluids. The duration of this contact may be relatively short, as is typical with wound dressings, or may be long term, as is typical with prosthetic heart valves implanted into the body of a recipient. Some articles such as catheters can have either short term or relatively long term contact. Other articles typically having relatively short term contact with the patient include, without limitation, burn dressings and contact lenses. Other articles typically having long term contact with a patient include, without limitation, implanted prostheses.

Contact of articles with bodily fluids creates a risk of infection. This risk can be very serious and even life threatening. In addition, considerable costs, and longer or additional hospital stays may result due to infection. For example, infections associated with dressings can increase the seriousness of the injury for burn victims. Also, infection associated with an implanted prosthesis can necessitate replacement of the device.

Infections are a particularly common complication resulting from the use in hospitals of percutaneous devices such as catheters. Infections related to catheter use can result from intracutaneous invasion during catheter insertion or from invasion by way of the exit site during use. Adherence of bacteria to the catheter surface complicates treatment of the infection.

Prostheses, i.e., prosthetic articles, are used to repair or replace damaged or diseased organs, tissues and other structures in humans and animals. Prostheses generally must be biocompatible since they are typically implanted for extended periods of time. Examples of prostheses include, without limitation, prosthetic hearts, prosthetic heart valves, ligament repair materials, vessel repair and replacement materials, stents, and surgical patches. A variety of prostheses may incorporate tissue as at least a component of the prosthesis.

Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a mechanical or bioprosthetic valve. Another technique uses an annuloplasty ring to provide structural support to the natural annulus of the native valve.

Prosthetic Valve Endocarditis (PVE) is an infection that can be associated with a heart valve prosthesis. Bacteria can form colonies at the surgical site associated with the implant and in the fabric of the sewing cuff of the valve prosthesis. The deposition of proteins onto the sewing cuff material also is associated with the attachment of bacteria and other pathogens. For this reason, heart valve recipients are cautioned regarding activities that may introduce bacteria into the bloodstream, such as dental work. For bioprosthetic replacement valves, PVE also is associated with the leaflet portion of the valve as well as the sewing cuff portion of the valve.

PVE can be caused by gram-negative bacteria, gram-positive bacteria, fungi or yeast. PVE caused by gram-positive bacteria is particularly prevalent. Diagnosis is based generally on two positive blood cultures for the same organism along with compatible clinical symptoms. Certain organisms are difficult to culture, however, which can complicate diagnosis.

With respect to replacement heart valves, care must be taken to ensure sterility during production and to prevent contamination during the replacement valve implantation process. For example, to ensure sterility or to reduce perioperative contamination, some surgeons apply antibiotics to the prosthesis prior to implantation. These techniques, however, have relatively short-term effectiveness. In spite of these efforts, PVE occurs in about 2 percent to 6 percent of patients.

Typically, infections occurring within the first 60 days after valve replacement are termed early onset PVE while infections occurring more than 60 days after valve implantation are termed late onset PVE. Mortality rates for early onset PVE may range from 30 percent to 80 percent. Mortality rates for late onset PVE can be greater than 20 percent. These high mortality rates emphasize the seriousness of these infections. Similar infections are associated with other prostheses.

SUMMARY OF THE INVENTION

In a first aspect the invention pertains to a method for preparing a medical article comprising biocompatible material, the method comprising:

combining a metal composition and the biocompatible material in a solution under reducing conditions, where the reducing conditions induce a reaction that results in deposition of antimicrobial metal in association with the biocompatible material.

In another aspect, the invention pertains to a method for preparing a medical article comprising biocompatible material, the method comprising:

combining a chemical reducing agent, a metal composition and the biocompatible material in a solution, where the chemical reducing agent induces a reaction that results in the deposition of antimicrobial metal in association with the biocompatible material.

In a further aspect, the invention pertains to a method for preparing a medical article, the method comprising:

illuminating a solution comprising an antimicrobial metal composition, the solution being in contact with biocompatible material, where the illumination results in the deposition of elemental antimicrobial metal, the antimicrobial metal being associated with the biocompatible material.

In addition, the invention pertains to a method for forming a medical article including a biocompatible material associated with an antimicrobial elemental metal, the method comprising:

electroplating an antimicrobial elemental metal onto the biocompatible material.

Furthermore, the invention pertains to a medical article comprising:

a material associated with an antimicrobial elemental metal, the material being selected from the group consisting of polymers and ceramics.

In another aspect, the invention pertains to a method of producing a medical article, the method comprising physically associating antimicrobial metal with another material in the formation of a biocompatible material. The physical association can be performed by forming, such as by weaving or knitting, thread, yarn or fibers into a fabric. Alternatively, the physical association can be performed by associating a metal leaf onto a biocompatible material. The fabric can comprise silver wire in some embodiments. In some embodiments, the physical association is performed by combining an antimicrobial metal composition with a polymer.

Moreover, the invention pertains to a medical article comprising fabric, the fabric comprising threads, fibers or yarns associated with a first antimicrobial metal and threads, fibers or yarns associated with a second elemental metal interspersed with the threads, fibers or yarns associated with the first antimicrobial elemental metal, where the second elemental metal alters the dissociation rate of the antimicrobial elemental metal when the fabric contacts an aqueous solution.

Furthermore, the invention pertains to a method for forming a medical article, the method comprising:

incorporating a fabric into the medical device, the fabric including thread, yarn, filaments or fibers having an associated antimicrobial elemental metal.

The invention also pertains to a medical article including fabric with associated antimicrobial elemental metal, the fabric having physical alterations to increase the surface area of the antimicrobial elemental metal.

In another aspect, the invention pertains to a method for forming a medical article, the method comprising:

depositing an antimicrobial elemental metal in association with a biocompatible material to form an amorphous deposit of elemental metal.

Moreover, the invention pertains to a medical article comprising:

a biocompatible material having an associated antimicrobial elemental metal and a second elemental metal in electrochemical contact with the antimicrobial elemental metal where the second elemental metal is selected to yield a desired dissociation rate for the antimicrobial elemental metal when the biocompatible material is in contact with bodily fluids.

In addition, the invention pertains to a method for forming a medical article, the method comprising:

associating a biocompatible material with a plurality of elemental metals, the plurality of elemental metals including antimicrobial elemental metal and a second elemental metal in electrochemical contact with the antimicrobial elemental metal where the second elemental metal is selected to yield a desired dissociation rate for the antimicrobial elemental metal when the biocompatible material is in contact with bodily fluids.

In another aspect, the invention pertains to a method for preparing a medical article, the method comprising:

contacting the medical article in vitro with an oxidizing agent, the medical device comprising an antimicrobial elemental metal.

Furthermore, the invention pertains to a method for producing a medical device, the method including:

reducing a metal compound associated with a biocompatible material to form an elemental metal associated with the biocompatible material.

In another aspect, the invention pertains to a prosthesis having a surface entirely associated with silver.

DETAILED DESCRIPTION OF THE PREFERRED EMBODIMENTS

New approaches are described to associate antimicrobial metal with medical articles that contact bodily fluids. The association of antimicrobial elemental metal with the medical articles inhibits the microbial colonization of the article. Suitable antimicrobial metals include, for example, Ag, Au, Pt, Pd, Ir, Cu, Sn, Sb, Pb, Bi, Zn and combinations thereof. The effectiveness of antimicrobial elemental metals is thought to be due to the formation of corresponding metal ions. Approaches are described for adjusting the dissociation or ionization rate of the antimicrobial metal to achieve a desired degree of antimicrobial effectiveness.

A variety of medical articles can be used to contact bodily fluids of a patient. Relevant biocompatible medical articles generally incorporate a biocompatible material which is intended to contact the patient's biological fluids and/or tissues. Bodily fluids include, for example, blood, plasma, serum, interstitial fluids, saliva and urine. The patient can be an animal, especially a mammal, and preferably is a human.

The antimicrobial metal can be associated with a portion or all of the surface of the medical device. In particular, a prosthesis, such as a heart valve, valved grafts, vascular grafts, pacemaker, defibrillator, conducting leads, or annuloplasty ring, can be formed with essentially the entire surface directly associated with an antimicrobial elemental metal, such as silver (Ag). Alternatively, selected partial or localized portions of the prosthesis surface can be directly associated with the antimicrobial metal. For example, pivot guards and/or the outer diameter of a heart valve prosthesis can be associated with the metal. In some embodiments, only parts of the prosthesis that contact tissue are associated with antimicrobial metal. The heart valve prosthesis can be a mechanical heart valve prosthesis or a tissue based heart valve prosthesis, a biosynthetic heart valve or a combination thereof.

Several approaches are described for associating antimicrobial metal with tissue and/or other biocompatible materials. A first approach involves the reaction of metal solutions with a chemical reductant, such as unreacted crosslinking agent, which may be present in or added to the biocompatible material. A second approach involves photoreduction of metal compounds in the presence of a biocompatible material. Also, elemental metal can be deposited onto materials by electroplating. In addition, threads or the like coated with antimicrobial metal can be woven, knit or otherwise formed into fabric to achieve a higher surface area relative to fabric coated directly with antimicrobial metal.

Multiple elemental metals can be codeposited in electrical contact such that the ionization of the antimicrobial elemental metal is altered by the presence of the other metal. Thus, the ionization rate can be adjusted to a more desirable value using codeposition of metals. Alternatively, the ionization rate can be altered by treating the surface of the deposited metal. In particular, the surface of the deposited metal can be oxidized.

The formation of antimicrobial elemental metal on biocompatible material, such as tissue, can provide relatively long term protection from infection as well as directed protection for shorter periods. Long term protection is especially important for the function of prostheses and the like which remain in contact with a patient's bodily fluids for an extended period of time. A combination of deposited antimicrobial agents can be more effective than a single antimicrobial agent.

While reducing the risk from infection, the patient's plasma levels of the corresponding metal ions should stay safely below toxic levels. Healthy humans generally have, for example, plasma levels of Ag of about 0.2 $\mu$g/l to about 10 $\mu$g/l, where 10 $\mu$g/l corresponds to about 0.01 ppm or 10 ppb. In the blood, silver ions are carried by high molecular weight proteins, such as glutathione and transferring. Silver cations are removed from the body with about 90 percent being excreted in bile and significant amounts being excreted in urine. Plasma levels of silver in sheep resulting from implantation of silver coated polyester have been evaluated. In these studies serum silver levels are well below the lowest reported levels causing toxic effects. See, K. S. Tweden et al., J. of Heart Valve Disease, 6:553–561(1997).

Serum silver ion concentrations of about 300 ppb have been associated with toxic symptoms including argyria in gingiva and cheeks, nephrotic syndrome and leukopenia. Silver ion concentrations of about 40 $\mu$mol/l (about 4 mg/l) are known to cause rapid cell death. Therefore, it is preferable to keep silver and other metal ion concentrations in the blood stream safely below toxic levels and preferably below levels where any symptoms are observable.

A. Biocompatible Article

Relevant biocompatible devices or articles include all medical articles that contact bodily fluids. These articles can be organized roughly into three groups: implanted (implantable) devices, percutaneous devices and cutaneous devices. Implanted devices broadly include articles that are fully implanted in a patient, i.e., are completely internal. Percutaneous devices include items that penetrate the skin, thereby extending from outside the body into the body. Cutaneous devices are used superficially, for example, at a wound site or at a moist membrane.

Implanted devices include, without limitation, cardiovascular prostheses and other types of prostheses such as pacemakers, pacing leads, defibrillators, transplant organs such as artificial hearts, ventricular assist devices, anatomical reconstruction prostheses such as breast implants, heart valve prostheses, cardiovascular repair patches such as pericardial patches, coronary stents, vascular grafts or conduits, biological conduits, pledgets, sutures, annuloplasty rings, stents, staples, valved grafts, vascular grafts, orthopedic, spinal implants, maxillofacial reconstruction plating, dental implants, intraocular lenses, clips, sternal wires, bone, skin, ligaments, tendons, and combinations thereof. Percutaneous devices include, without limitation, catheters of various types, cannulas, drainage tubes such as chest tubes, surgical instruments such as forceps, retractors, needles, and gloves, and catheter cuffs. Catheters can be used for accessing various bodily systems such as the vascular system, the gastrointestinal tract, or the urinary system. Cutaneous devices include, without limitation, skin grafts, burn dressings, wound dressings of all types, and contact lenses. These biocompatible articles can be made from the biocompatible materials described below.

B. Biocompatible Material

Appropriate biocompatible materials include natural materials, synthetic materials and combinations thereof. Natural, i.e., biological, material for use in the invention includes relatively intact (cellular) tissue as well as decellularized tissue. These tissues may be obtained from, for example, natural heart valves; portions of natural heart valves such as roots, walls and leaflets; pericardial tissues such as pericardial patches; connective tissues; fascia; bypass grafts; tendons; ligaments; skin patches; blood vessels; cartilage; dura matter; skin; bone; umbilical tissues; and the like.

Natural tissues are derived from a particular animal species, typically mammalian, such as human, bovine, porcine, seal or kangaroo. These natural tissues generally include collagen-containing material. Natural tissue is typically, but not necessarily, soft tissue. Appropriate tissues also include tissue equivalents such as tissue-engineered material involving a cell-repopulated matrix, which can be formed from a polymer or from a decellularized natural tissue. Tissue materials are particularly useful for the formation of tissue heart valve prostheses.

Tissues can be fixed by crosslinking. This provides mechanical stabilization, for example, by preventing enzymatic degradation of the tissue. Glutaraldehyde is typically used for fixation, but other difunctional aldehydes or epoxides can be used. Tissues can be used in either crosslinked or uncrosslinked form, depending on the type of tissue, the use and other factors.

Relevant synthetic materials include, for example, polymers, metals and ceramics. Appropriate ceramics include, without limitation, hydroxyapatite, alumina and pyrolytic carbon. Appropriate metals include metals or alloys approved for medical use including, for example, steel and titanium. Appropriate synthetic materials include hydrogels and other synthetic materials that cannot withstand severe dehydration.

Polymeric materials can be fabricated from synthetic polymers as well as purified biological polymers. The polymeric materials can be woven into a mesh to form a matrix or substrate. Alternatively, the synthetic polymer materials can be molded or cast into appropriate forms.

Appropriate synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. Conductive polymers include, for example, doped polymers of poly(sulfur nitride), polyacetylene, poly(p-phenylene), poly(phenylene sulfide) and polypyrrole. Other suitable polymers include resorbable polymers such as dextran, hydroethyl starch, gelatin, derivatives of gelatin, polyvinylpyrrolidone, polyvinylalcohol, poly[N-(2-hydroxylpropyl) methacrylamide], polyglycols, polyesters, poly (orthoesters), poly(ester amides), polyanhydrides. Resorbable polyesters include, for example, poly (hydroxy acids) and copolymers thereof, poly($\epsilon$-caprolactone), poly (dimethyl glycolic acid), and poly (hydroxy butyrate). Preferred resorbable polymers include, for example, D, L-polylactic acid, L-polylactic acid, poly(glycolic acid), and copolymers of L-lactic acid, D-lactic acid and glycolic acid.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349–357 (1996). Suitable biological polymers include, without limitation, collagen, elastin, silk, keratin, gelatin, polyamino acids, cat gut sutures, polysaccharides (e.g., cellulose and starch) and copolymers thereof.

Biocompatible materials can include a combination of the various natural materials and synthetic materials described above. For example, some prosthesis are made entirely from tissue, or tissue with fabric, such as sewing rings, or metal components. Other relevant prostheses are made completely from metal, ceramics or a combination of metal, ceramics and, optionally, additional natural or synthetic materials. Mechanical heart valves, artificial hearts, ventricular assist devices, coronary stents, annuloplasty rings, conducting leads and defibrillators are relevant products, which generally are made from metallic, polymeric and/or ceramic components.

C. Deposited Antimicrobial Metal

The approaches for applying deposits of antimicrobial metal can be broadly classified according to whether the deposition takes place from a vapor phase, a solid phase, or from a liquid phase. Antimicrobial metals include, for example, silver, gold, platinum, palladium, iridium, copper, tin, lead, antimony, bismuth and zinc. Certain types of deposition approaches may be especially suitable to associate antimicrobial metal with particular types of corresponding biocompatible materials. Four particular approaches are described for the preparation of biocompatible materials that have a deposit of antimicrobial elemental metal for use in the biocompatible article. The first three approaches are solution based methods to treat finished medical devices, subassemblies or components of medical devices. The fourth method can use either a solution based method, a solid phase method, or a vapor phase method to prepare components that are physically associated to form the material, such as weaving thread or the like into a fabric.

To determine the amount of metal to deposit, the rate of dissolution can be taken into consideration. The environment in which the biocompatible material is placed can influence the rate of dissolution. Given a particular rate of dissolution, the amount of deposited metal establishes the length of time over which metal is available for microbial inhibition. Processing considerations such as time, cost and deposition limitations may influence the amount of metal deposited. Toxicity issues also may dictate the deposition of lesser amounts of elemental metal.

Some of the procedures described herein involve contacting the biocompatible material with a metal salt solution at some point during the processing. Some metal ions generally associate themselves with the biocompatible material during this contact. This additional form of treatment is a natural part of the relevant procedures described herein. Thus, the extent of reduction can be varied to alter the amount of ionic species immediately available relative to the amount of reduced antimicrobial metal available over time.

With any method of deposition, the amount of deposited metal should not interfere significantly with important functionality of the biocompatible material. The amount of antimicrobial metal, such as silver, incorporated into the medical article generally is greater than about 0.01 mg per gram of dry biocompatible material, and preferably greater than about 0.05 mg per gram of dry biocompatible material, and more preferably from about 0.1 mg to about 20 mg per gram of dry biocompatible material. Alternatively, the proportion of antimicrobial metal could be higher if significant portions of the medical article are fabricated from the antimicrobial metal. When incorporated into a medical article, the proportion of elemental metal relative to the total quantity of biocompatible materials can be less than the above range since portions of the biocompatible materials may not have deposits of elemental metal.

In general, the biocompatible material can be subjected to deposition of elemental metal prior to, during or after processing into a biocompatible article. For example, to form a bioprosthetic or mechanical heart valve with a fabric component, the tissue or mechanical component and the fabric can be separately subjected to deposition of antimicrobial elemental metal using conditions suitable for each material. Similarly, only the tissue or mechanical components or only the fabric can be subjected to antimicrobial metal deposition. Following the desired deposition of antimicrobial metal, the tissue/mechanical component and the fabric component can be combined. Alternatively, the tissue/mechanical component and the fabric component can be formed into a biocompatible article followed by the deposition of antimicrobial elemental metal using a suitable method for the different materials.

1. Chemical Reduction

In this approach, the biocompatible material is contacted with a solution including an antimicrobial metal composition. The metal compound generally is relatively soluble in the solvent being used. Suitable silver compounds include, for example, silver nitrate. Generally, the solution is relative concentrates such that the process proceeds at a reasonable rate. A reducing agent is then added to the solution. The corresponding metal is then deposited upon reduction onto the biocompatible material, as an elemental metal or as a less soluble metal compound.

The solvent is selected such that the biocompatible material is not degraded by the solvent. Suitable solvents are generally aqueous although other solvents, such as alcohols, can be used. The metal compound should be sufficiently soluble such that the concentration of metal compound in solution provides a desirable level of elemental metal deposition upon exposure to the reducing agent.

Suitable reducing agents include, for example, aldehydes, sodium borohydride, $H_2$ and CO for reduction of a variety of metals. Gaseous reducing agents can be bubbled through the solution. In particular, aldehydes are known to reduce silver ions to elemental silver. The traditional silver compound for the reduction with aldehydes is ammoniacal silver hydroxide ($Ag(NH_3)_2OH$), "Tollen's reagent." Aldehydes can be supplied as partly unreacted multifunctional aldehyde compounds, such as crosslinking agents. Similarly, a palladium chloride solution can be reduced to form palladium metal using hydrogen or carbon monoxide (CO), which can be bubbled into the solution. Elemental copper can be precipitated from copper solutions by the addition of aluminum, iron or zinc particles.

Generally, the reduction process produces elemental metal in association with the substrate. Alternatively, the reduction converts the metal to a less soluble cation. Then, a metal compound precipitates onto the substrate. For example, cupric ions ($Cu^{+2}$) are reduced by aldehydes to form cuprous ions ($Cu^{+1}$). A traditional reagent for this reaction is cupric tartarate ($CuC_4O_6H_4$), "Fehling's solution." Generally, insoluble CuO is formed.

When processing tissue, it is preferred to keep the pH between values of about 4 and about 11, and more preferably between about 7.0 and about 8.0, to the extent that the pH can be adjusted within the particular processing approach. The solution can include a buffer with a pH in a desirable range. Suitable buffers can be based on, for example, the following compounds: phosphate, borate, bicarbonate, carbonate, EDTA acetate, cacodylate, citrate, and other organic buffers such as tris(hydroxymethyl)amino methane (TRIS), N-(2-hydroxyethyl) piperazine-N'-(2-ethanesulfonic acid) (HEPES), and morpholine propanesulphonic acid (MOPS). Some buffers may be unsuitable for use with certain metal solutions. Ionic strength can be adjusted, if desired, by the addition of inert salts, the identity of which generally depends on the nature of the deposition process and the corresponding compositions.

2. Photochemical Deposition

Many silver compounds are subject to photochemical reduction. To perform the photochemical deposition, a sufficiently soluble silver compound is dissolved in a solvent. Suitable solvents are inert with respect to the biocompatible material. Suitable silver compounds include, for example, silver nitrate. The biocompatible material is placed in the solution and exposed to either natural or artificial light to reduce the metal compound to elemental silver. The elemental silver is deposited on the biocompatible materials, which can act as a nucleation site. Suitable solvents and buffers are as described above.

3. Electrochemical Deposition

To achieve electrochemical deposition, the biocompatible material must be rendered electrically conducting. Thus, if the material is not inherently electrically conducting, the material can be surface treated with graphite or the like to render the material electrically conducting. Biocompatible materials of particular interest include, as a component, polymers, ceramics and other metals such as titanium, cobalt, alloys thereof and Elgiloy®, a cobalt-chromium-nickel-molybdenum-iron alloy. A variety of suitable polymers (natural and synthetic) are described above.

Electrochemical deposition involves the application of a voltage in order to electroplate elemental metal in contact with the biocompatible material. The biocompatible material functions as a cathode. The voltage required depends on the counter reaction and the concentrations of ions in solution. Selection of the metal composition influences the effectiveness of the plating process. The electroplating generally is performed with an aqueous solution of a water soluble compound of the desired metal.

4. Physical Association

In an embodiment of a solid phase method, elemental metal can be associated with a biocompatible material by direct physical association of the metal with the material. For example, a metal leaf can be pressed onto the biocompatible material. Alternatively, wire made from antimicrobial metal can be woven into the material, such as a fabric, or sewn through the material, such as a tissue. In a further alternative embodiment, increasing proportions of the medical device can be fabricated from antimicrobial metal, up to and including the full device.

Similarly, an antimicrobial metal composition and/or elemental metal can be mixed with a polymer during formation. Multiple compounds and/or elemental metals can be mixed together to achieve a desired amount of effectiveness. The polymer can be formed into thread or into sheets of material for formation into a medical article or a component or subassembly. The antimicrobial metal can leach from the polymer during use. In particular, an antimicrobial elemental metal composition can be mixed with a hydrogel, such as a partially sulfonated hydrogel or a hydrogel with an appropriate counter ion or ligand that would reversibly bind the appropriate metal, that is applied as a coating to the biocompatible material, such as a fabric.

Metal coated fabric can be produced by deposition of metal onto the fabric. A higher surface area per weight of elemental metal can be obtained by coating the threads, yarn, filaments or fibers prior to forming the fabric. In other words, the fabric is woven, knitted or otherwise formed from metal coated thread, yarn, filament, fiber or the like. The metal can be deposited in the form of elemental metal and/or as a metal composition.

The fabric made from the metal coated threads maintains the porous nature of the fabric. The tightness of the weave determines the degree of porosity. The porosity may be advantageous for certain applications, in particular where tissue ingrowth is desirable. For example, the fabric can be used to form a sewing ring for a medical device, such as a heart valve prosthesis. The threads can be woven, knitted or otherwise formed into fabric using a variety of processes including conventional processes.

The metal can be deposited on the thread using either vapor or solution based methods. The solution based methods described above, for example, can be used. Vapor phase methods include, for example, vapor deposition, metal plasma deposition, sputtering and magnetron sputtering. Vapor phase deposition techniques generally require varying degrees of vacuum, i.e., low pressure.

Vapor deposition can simply involve directing vaporized metal toward the substrate to be metalized. Vapor deposition preferably is performed using ion-beam-assisted deposition (IBAD) under high vacuum as described, for example, in U.S. Pat. No. 5,474,797 to Sioshansi et al., incorporated herein by reference, although other vapor deposition techniques are within the invention. IBAD involves an evaporator that forms a vapor of the desired metal. The metal vapor is delivered to the substrate by a beam of ions formed from one or more gases.

D. Codeposition of Elemental Metals

Multiple elemental metals can be deposited such that the different elemental metals are or are not in electrical contact with each other. The oxidation potential of one metal may influence the rate of oxidation of the other metal. In this way, the rate of oxidation of one metal can be accelerated or slowed by the selection of a second metal. An additional metal can also be selected also to supply beneficial effects. In particular, an additional elemental metal can itself be an antimicrobial elemental metal, such as the combination of silver and copper. Alternatively, an additional elemental metal can be an anticalcific elemental metal. Anticalcific metals include, for example, aluminum, iron, manganese, zinc, gallium, lanthanum and beryllium.

If multiple elemental metals are in electrical contact, one metal generally is stabilized in its elemental form while the oxidation of the other metal is enhanced. In other words, the less easily oxidized metal is generally preserved by the preferential oxidation of the other metal until the more easily oxidized metal is consumed or no longer in electrical contact with the more stable metal. Thus, the stabilized metal may not be as effective at imparting beneficial effects while the other metal is present. After the more easily oxidized metal is consumed, the more stabilized metal is oxidized to impart the desired effect. For example, a combination of silver and copper deposits would result in the faster ionization of copper and the slower ionization of silver.

Even if the elemental metals are not in direct physical contact, the presence of a second elemental metal may influence the oxidation rate and corresponding effectiveness of the first elemental metal as an antimicrobial agent and vice versa. This influence is the result of the local presence of ions and atoms of the other metal.

If one or more antimicrobial elemental metals are in electrochemical contact (electrical contact and/or chemical contact) with one or more other metals, the additional other metal(s) can introduce another activity and/or can adjust the delivery rate of the antimicrobial elemental metal(s).

For vapor phase techniques, the deposition of multiple metals can be performed sequentially or simultaneously. Specifically, multiple metals can be placed in successive layers, the metals can be deposited simultaneously to create an amorphous surface, and/or the metals can be patterned onto the substrate such that each metal contacts a selected portion of the substrate. In addition, different elemental metals can be incorporated onto different portions of one or more sections of biocompatible material for incorporation as components into a single medical article.

Generally, solution-based methods involve the sequential deposition of the elemental metals. Solution phase techniques can be used to pattern a single portion of biocompatible material if some effort is applied to contact only the desired portion with the solution. The solution can be applied, for example, by dipping, spraying or submerging the biocompatible material The order of deposition may be influenced by the method or methods used to deposit the elemental metals if, for example, one elemental metal is unstable during the deposition of the second metal. The placement of the multiple metals generally is influenced by the impact on the antimicrobial effectiveness resulting from the particular relationship between the metals, as described above.

E. Control of Ionization Through Surface Treatment

The surface of the metal deposits can be subjected to oxidizing conditions to enhance the dissolution of the antimicrobial elemental metal. Oxidation is a necessary step to the solubilization of the metal as a metal compound or metal ion. In particular, with antimicrobial elemental metals, it may be desirable to have an enhanced antimicrobial impact during the initial use of the biocompatible article as a result of the oxidized surface of the metal. Long term antimicrobial effectiveness results from the remaining elemental metal. The degree of oxidation can be adjusted to yield the desired degree of dissolution of the elemental metal.

The oxidizing conditions can be supplied by a chemical oxidizing agent or by a physical treatment. Suitable chemical oxidizing agents include, for example, hydrogen peroxide, super oxides, oxygen radicals, ozone, hydrogen sulfide, permanganate, Grignard reagents, metal ions with suitable redox potentials, sulfur and nitric acid. The chemical oxidizing agents can be supplied in an aqueous or nonaqueous solution.

Suitable physical oxidation treatments include, for example, flame treatment. With flame treatment, the biocompatible material with the elemental metal deposits are passed near a flame. The materials should not pass too close to the flame since the flame could damage the biocompatible material. On the other hand, the materials should not pass too far from the flame or the flame may be ineffective at oxidizing the elemental metal. In the presence of methane or hydrogen, contact with the flame can be reducing. Thus, a metal compound deposited on a substrate can be converted partially or totally to elemental metal by reduction caused by the flame.

Alternatively, a biocompatible material such as a fabric with associated antimicrobial metal can be subjected to mechanical treatment to increase the dissociation rate. For example, the biocompatible material can be cut to increase the surface area. The cuts can be made in a variety of ways as long as the mechanical durability of the biocompatible material is not compromised. Similarly, the biocompatible material can be mechanically abraded or scored such that the surface becomes rough, thereby increasing the surface area.

F. Processing Considerations

In general, the biocompatible material can be subjected to elemental metal deposition prior to, during, or following processing into a biocompatible article. For example, a heart valve prosthesis can be treated to deposit antimicrobial metal either before or after attachment of a sewing cuff. The mechanical properties of the biocompatible material, especially tissue, should not be significantly degraded by the antimicrobial metal deposition. In particular, material properties such as flexural modulus, stress and strain responses and mechanical strength should not deteriorate significantly, and the material preferably maintains its flexibility.

There are certain situations where multiple biological activities are desirable. In these situations, materials can be made by forming a bioactive coating on a base material, where the bioactive coating can include, for example, cell adhesion molecules, such as fibronectin or other arginine-glycine-aspartic acid sequence containing peptides, anticoagulants such as heparin and hirudin, growth factors, chemotactants, and combinations thereof.

Articles with bioactive coatings then can be subjected to further application of antimicrobial elemental metal using the techniques described herein. In some cases, the order of the application of the antimicrobial metal and the other bioactive material can be reversed. If appropriate, the application of the antimicrobial metal and other bioactive material can be performed simultaneously. Performance may be influenced by the order of application of the different active agents, and in such cases, the order of application can be selected based on performance considerations. Empirical evaluation of these factors can be performed, if desired.

G. Combination of Approaches

With implanted heart valve prostheses, the two month period immediately following implantation is a particularly significant period with respect to the prevention of infection since the greatest number of cases of PVE typically occur in this time period. Nevertheless, the risk of infection due to prosthesis implantation continues for the duration of the implant. It may be possible to improve the overall effectiveness of antimicrobial treatments by combining two or more antimicrobial agents. For example, the deposition of multiple antimicrobial elemental metals was described above.

Alternatively, metal compounds with antimicrobial activity can be deposited along with the elemental metal. These metal compounds can be deposited by precipitation of the compound from a solution of a corresponding soluble metal compound by the addition of a precipitation agent, generally an appropriate anion or a reducing agent to form a lower oxidation state metal ion. Deposition of antimicrobial metal compounds is described further in copending and commonly assigned U.S. patent application Ser. No. 08/974,992 to Ogle et al., entitled "Medical Article with Adhered Antimicrobial Metal," incorporated herein by reference. A particularly preferred combination is elemental silver combined with a silver compound such as silver chloride.

In particular, it may be desirable to combine one deposited antimicrobial metal compound having relatively high metal ion loss rate over the first two to three month period with an antimicrobial elemental metal that provides continued antimicrobial effectiveness for a year or more. An additional antimicrobial metal compound with a higher solubility can be deposited, providing an especially large amount of antimicrobial ions during the first days or weeks from the implantation. Additional or alternative combinations of antimicrobial agents can be used, as desired.

With any of the methods involving multiple antimicrobial agents, the agents should be deposited such that the device maintains adequate mechanical properties. For example, heart valve prostheses have components that must flex during use. In addition, different parts of the biocompatible material can be associated with distinct antimicrobial agents, either metal compounds or elemental metal, to ensure adequate mechanical properties of the prosthesis. Similarly, whether one or more antimicrobial agents are deposited, only a portion or certain parts of the biocompatible material may be associated with the antimicrobial agents. For example, the entire device can be covered with one antimicrobial agent while only select portions are covered with a second antimicrobial agent. Further, portions of the device could have one or more antimicrobial agents, or not be covered at all.

Furthermore, the procedures described herein can be combined with other approaches to reduce microbial infection. For example, glutaraldehyde treatment is effective in reducing microbial contamination of medical articles. Glutaraldehyde can be used effectively even if it is not needed as a crosslinking agent. Similarly, immersing a medical article in alcohol or an aqueous alcohol solution can reduce microbial contamination.

Also, commonly assigned U.S. patent application Ser. No. 08/787,139 to Tweden et al., "Medical Article with Adhered Antimicrobial Metal Ions and Related Methods," incorporated herein by reference, discloses a method of associating antimicrobial metal cations with exogenous storage structures, for example, metal storage proteins such as ferritin. Exogenous storage structures are not native or inherent to the biocompatible material. The exogenous storage structures containing antimicrobial ions are then bound to biocompatible material. The procedures based on exogenous storage structures can be combined with the procedures described herein for depositing elemental metal and/or insoluble metal compounds in association with biocompatible material. The association of the exogenous storage structures with the biocompatible material can be performed before, during or after deposition of metal and/or metal compounds into or onto the biocompatible material.

H. Combination with Anticalcification Agents

Polyvalent metal cations such as $Fe^{+3}$ and $Al^{+3}$ have been shown to be useful in reducing calcification that is associated with implanted prostheses. As described above, anticalcification elemental metals can be codeposited with antimicrobial elemental metals. The anticalcification elemental metal can be a source of anticalcific cations. The elemental metals can be deposited in such a way that both the antimicrobial metal and the anticalcific metal are effective over relevant time periods required for antimicrobial effectiveness and anticalcific effectiveness. Furthermore, the antimicrobial metal and anticalcific metal can be deposited on different portions of the prosthesis that are particularly sensitive to each effect.

In addition, exogenous storage structures have been shown to be useful in delivering these polyvalent cations. See, commonly assigned and copending U.S. patent application Ser. No. 08/690,661 to Schroeder et al., entitled Calcification-Resistant Biomaterials," incorporated herein by reference. These exogenous storage structures with stored anticalcific ions can be combined with the deposits of antimicrobial elemental metal.

I. Storage, Packaging, Distribution and Use

Following deposition of desired antimicrobial agents, the biocompatible material, possibly formed into a medical article, is stored. The biocompatible material or device is stored under appropriate environmental conditions for the particular material or device without compromising the efficacy of the antimicrobial treatment. Preferred storage techniques minimize the risk of microbial contamination.

Still, due consideration should be given to possible loss over time of the deposited antimicrobial metal during storage. If excessive amounts of antimicrobial agent would be lost or absorbed into the storage environment, the storage time should be selected such that the amount of antimicrobial metal lost from the biocompatible material is within a satisfactory level.

For distribution, the medical articles are placed in sealed and sterile containers. The containers are generally dated such that the date reflects the maximum advisable storage time accounting for possible degradation of the antimicrobial agents as well as other factors. The containers are packaged along with instructions for the proper use and/or implantation of the medical device and along with appropriate and/or required labeling. The containers are distributed to health care professionals for use in appropriate medical procedures such as implantation of a prosthesis and the like.

The reduction of infection frequency is an important objective in the design of medical devices that contact bodily fluids. The methods disclosed herein expand the design options available to achieve this objective. In particular, the approaches described above are particularly advantageous for the processing of certain biocompatible materials and for the design of improved antimicrobial effectiveness over desired time frames. The antimicrobial metals associated with the substrates should inhibit microbial attachment, growth and/or colonization. Furthermore, these antimicrobial approaches provide for additional flexibility with respect to combinations with anticalcification agents. Antimicrobial metals have been shown to provide broad spectrum effectivity, are relatively cost effective with respect to antibiotics, and have demonstrated lower incidence of resistant strain development.

Although the present invention has been described with reference to preferred embodiments, workers skilled in the art will recognize that changes may be made in form and detail without departing from the spirit and scope of the invention.

What is claimed is:

1. A medical article comprising fabric, said fabric comprising first threads, fibers or yarns associated with a first elemental metal and second threads, fibers or yarns associated with a second elemental metal and not with the first elemental metal interspersed with said first threads, fibers or yarns associated with said first elemental metal, wherein the first threads, fibers or yarns are not associated with the second elemental metal and wherein said first elemental metal comprises an antimicrobial elemental metal and where said second elemental metal alters the dissociation rate of said first elemental metal when said fabric contacts an aqueous solution.

2. The medical article of claim 1 wherein said first antimicrobial elemental metal comprises silver and said second elemental metal comprises aluminum.

3. The medical article of claim 1 wherein said fabric has cuts to increase the surface area of said antimicrobial elemental metal.

4. The medical article of claim 1 wherein said first threads, fibers or yarns are associated with elemental metal by a method comprising:

depositing Simultaneously a plurality of elemental metals, at least one of which is an antimicrobial metal, in association with a biocompatible material to form an amorphous deposit of elemental metal.

5. The medical article of claim 1 wherein said fabric is treated by a method comprising:

contacting said medical article in vitro with an oxidizing agent selected from the group consisting of a flame, super oxides, oxygen radicals, ozone, hydrogen sulfide, permanganate, Grignard reagents, metal ions with suitable redox potentials, sulfur and nitric acid.

6. The method of claim 5 wherein said oxidizing agent comprises super oxides, oxygen radicals, ozone, hydrogen sulfide, permanganate, Grignard reagents, metal ions with suitable redox potentials, sulfur or nitric acid.

7. The method of claim 5 wherein said oxidizing agent comprises a flame.

8. The medical article of claim 1 wherein the fabric is porous.

9. The medical article of claim 3 wherein the mechanical durability of the fabric is not compromised.

10. The medical article of claim 4 wherein the deposition is performed by vapor phase deposition.

11. The medical article of claim 4 wherein the deposition is performed by ion-beam-assisted deposition.

12. The medical article of claim 4 wherein the plurality of metals comprises silver and aluminum.

\* \* \* \* \*